US007476535B2

(12) United States Patent
Khong et al.

(10) Patent No.: US 7,476,535 B2
(45) Date of Patent: Jan. 13, 2009

(54) TRP2 ISOFORM TRP2-6B CONTAINING HLA-A2 RESTRICTED EPITOPES

(75) Inventors: Hung Khong, Bethesda, MD (US); Steven A. Rosenberg, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 768 days.

(21) Appl. No.: 10/468,665

(22) PCT Filed: Mar. 15, 2002

(86) PCT No.: PCT/US02/07698

§ 371 (c)(1),
(2), (4) Date: Dec. 22, 2003

(87) PCT Pub. No.: WO02/074788

PCT Pub. Date: Sep. 26, 2002

(65) Prior Publication Data

US 2004/0116667 A1 Jun. 17, 2004

Related U.S. Application Data

(60) Provisional application No. 60/277,108, filed on Mar. 19, 2001.

(51) Int. Cl.
*C12N 15/00* (2006.01)
(52) U.S. Cl. .................. 435/320.1; 530/350; 536/23.5; 435/325; 435/372.3
(58) Field of Classification Search .................. 530/350, 530/300; 536/23.5; 435/320.1, 325, 372.3; 424/185.1, 277.1; 514/44
See application file for complete search history.

(56) References Cited

OTHER PUBLICATIONS

Skolnick et al. (Trends in Biotechnology, 2000; 18 (1): 34-39).*
De Plaen et al. (Immunogenetics. 1994; 40: 360-369).*
Houdebine (Journal of Biotechnology 1994, 34: 269-287).*
Verma et al. (Nature. 1997, 389: 239-242).*
Amalfitano et al. (Current Gene Therapy. 2002, 2: 111-133).*
Pandha et al. (Current Opinion in Investigational Drugs. 2000; 1 (1): 122-134).*
Lu et al. (Cancer Research 62: 5807-5812, 2002).*
Lollini et al. (Curr. Cancer Drug Targets. May 2005; 5 (3): 221-228).*
Lollini et al. (Trends Immunol. Feb. 2003; 24 (2): 62-66).*
Slinghuff et al. (Cancer Immunol. Immunother. Mar. 2000; 48 (12): 661-672).*
Bodey et al. (Anticancer Research. 2000; 20: 2665-2676).*
Boon (Advances in Cancer Research. 1992, 58: 177-210).*
Lee et al. (Journal of Immunology. 1999; 163: 6292-6300).*
Zaks et al. (Cancer Research. 1998; 58: 4902-4908).*
Gao et al. (Journal of Immunotherapy. 2000; 23: 643-653).*
Wang et al. (Exp. Opin. Biol. Ther. 2001; 1 (2): 277-290).*
Nichols et al. (J. Invest. Dermatol. Oct. 2003; 121 (4): 821-830).*
Birtle (BMC Genomics. Sep. 13, 2005; 6: 120; pp. 1-19).*
Bins et al. (J. Immunother. Feb.-Mar. 2007; 30 (2): 234-239).*
Bloom et al., "dentification of Tyrosinase-related Protein 2 as a Tumor Rejection Antigen for the B16 Melanoma," *J. Exp. Med.*, 1997, pp. 453-459, 185(3).
Brichard et al., "The Tyrosinase Gene Codes for an Antigen Recognized by Autologous Cytolytic T Lymphocytes on HLA-A2 Melanomas," *J. Exp. Med.*, 1993, pp. 489-495, 178.
Chen et al., "A Testicular Antigen Aberrantly Expressed in Human Cancers Detected by Autologous Antibody Screening," *Proc. Nat. Acad. Sci. USA*, 1997, pp. 1914-1918, 94.
Coulie et al., "A New Gene Coding for a Differentiation Antigen Recognized by Autologous Cytolytic T Lymphocytes on HLA-A2 Melanomas," *J. Exp. Med.*, 1994, pp. 35-42, 180.
Coulie et al., "A Mutated Intron Sequence Codes for an Antigenic Peptide Recognized by Cytolytic T Lymphocytes on a Human Melanoma," *Proc. Natl. Acad. Sci. USA*, 1995, pp. 7976-7980, 92.
Harada et al., "Use of an in Vitro Immunoselected Tumor Line Identify Shared Melanoma Antigens Recognized by HLA-A*0201-Restricted T Cells," *Cancer Research*, 2001, pp. 1089-1094, 61.
Hom et al., "Specific Release of Cytokines by Lymphocytes Infiltrating Human Melanomas in Response to Shared Melanoma Antigens, Journal of Immunotherapy," 1993, pp. 18-30, 13.
Ikeda et al., "Characterization of an Antigen That Is Recognized on a Melanoma Showing Partial HLA Loss by CTL Expressing an NK Inhibitory Receptor", *Immunity*, 1997, pp. 199-208, 6.
Kawakami et al., "Cloning of the Gene Coding For a Shared Human Melanoma Antigen Recognized by Autologous T cells Infiltrating into Tumor," *Proc. Nat. Acad. Sci.*, 1994, pp. 3515-3519, 91.
Kawakami et al., "Identification of a Human Melanoma Antigen Recognized by Tumor-Infiltrating Lymphocytes Associated with In Vivo Tumor Rejection," Proc. Nat. Acad. Sci., 1994, pp. 6458-6492, 91.
Kawakami et al., "Identification of Melanoma Antigens Recognized by T Lymphocytes and Their Use in the Immunotherapy of Cancer," Principle and Practice of Oncology Update, 1997, pp. 1-20 (Philadelphia: Lippincott-Raven).
Khong et al., "Pre-Existing Immunity to Tyrosinase-Related Protein (TRP)-2, a New TRP-2 Isoform, and the NY-ESO-1 Melanoma Antigen in a Patient with a Dramatic Response to Immunotherapy," *J. Immunol.*, 2002, pp. 951-956, 168(2).

(Continued)

*Primary Examiner*—Stephen L Rawlings
(74) *Attorney, Agent, or Firm*—Leydig, Voit & Mayer, Ltd.

(57) ABSTRACT

The present invention relates to a new and potent tumor antigen capable of causing T cells to elicit an immune response and methods of its use in the detection, prevention, and treatment of cancer, preferably melanoma, in mammals. More specifically, this invention relates to the identification of a novel tyrosinase-related protein 2(TRP2), specifically TRP2-6b protein, and peptides derived from said protein. The present invention therefore also relates to nucleic acid seciuences that encode the TRP2-6b protein or peptide fragments thereof.

5 Claims, 4 Drawing Sheets

OTHER PUBLICATIONS

Lupetti et al., "Translation of a Retained Intron in Tyrosinase-Related Protein (TRP 2 mRNA Generates a New Cytotoxic T Lymphocyte (CTL)-defined and Shared Human Melanoma Antigen Not Expressed in Normal Cells of the Melanocytic Lineage," *J. Exp. Med.*, 1998, pp. 1005-1016, 188(6).

Noppen, "Naturally Processed and Concealed HLA-A2.1-Restricted Epitopes from Tumor-Associated Antigen Tyrosinase-Related Protein-2", *Int. J. Cancer*, 2000, pp. 241-246, 87.

Noppen et al., "Identification of a New HLA-A*0201-Restricted T-Cell Epitope From the Tyrosinase-Related Protein 2 (TRP2) Melanoma Antigen," *Int. J. Cancer*, 2000, pp. 399-404, 87.

Parkhurst et al., "Identification of a Shared HLA-A*0201-Restricted T-Cell Epitope from the Melanoma Antigen Tyrosinase-related Protein 2 (TRP2)[1]," *Cancer Research*, 1998, pp. 4895-4901, 58.

Pisarra et al., "Human Melanocytes and Melanomas Express Novel mRNA Isoforms of the *Tyrosinase-Related Protein-2/DOP Achrome Tautomerase* Gene: Molecular and Functional Characterization," *J. Invest. Dermatol.*, 2000, pp. 48-56, 115.

Rammensee et al., "MHC Ligands and Peptide Motifs: First Listing," *Immunogenetics*, 1995, pp. 178-228, 41.

Reynolds et al., "HLA-Independent Heterogeneity of CD8+ T Cell Responses to MAGE-3, Melan-A/MART-1, gp100, Tyrosinase, MC1R, and TRP-2 in Vaccine-Treated Melanoma Patients[1]," *J. Immunol.*, 1998, pp. 6970-6976, 161(12).

Robbins et al., "Cloning of a New Gene Encoding an Antigen Recognized by Melanoma-Specific HLA-A24-Restricted Tumor-Infiltrating Lymphocytes," *J. Immunol.*, 1995, pp. 5944-5950, 154(11).

Robbins et al., "A Mutated β-Catenin Gene Encodes a Melanoma-specific Antigen Recognized by Tumor Infiltrating Lymphocytes," *J. Exp. Med.*, 1996, pp. 1185-1192, 183.

Rosenberg et al., "Use of Tumor-Infiltrating Lymphocytes and Interleukin-2 In The Immunotherapy of Patients With Metastatic Melanoma," *New England J. Med.*, 1988, pp. 1676-1680, 319(25).

Rosenberg et al., "Treatment of Patients with Metastatic Melanoma With Autologous Tumor-Infiltrating Lymphocytes and Interleukin 2," *Journal of the National Cancer Institute*, 1994, pp. 1159-1166, 86(15).

Rosenberg, "A New Era for Cancer Immunotherapy Based on the Genes that Encode Cancer Antigens," *Immunity*, 1999, pp. 281-287, 10.

Strum et al., "Chromosomal Structure of the Human TYRP1 and TYRP2 Loci and Comparison of the Tyrosinase-Related Protein Gene Family," *Genomics*, 1995, pp. 24-34, 29.

Sun et al., "Identification of a New HLA-A*0201-Restricted T-Cell Epitope From The Tyrosinase-Related Protein 2 (TRP2) Melanoma Antigen," *Int. J. Cancer*, 2000, pp. 399-404, 87.

Takahashi et al., "Identification of MAGE-1 and MAGE-4 Proteins in Spermatogonia and Primary Spermatocytes of Testis[1]," *Cancer Research*, 1995, pp. 3478-3482, 55.

Van Den Eynde, et al., "T Cell Defined Tumor Antigens," *Curr. Opin. Immunol.*, 1997, pp. 684-693, 9.

Wang et al., "Identification of a Gene Encoding a Melanoma Tumor Antigen Recognized by HLA-A31-restricted Tumor-infiltrating Lymphocytes," *J. Exp. Med.*, 1995, pp. 799-804, 181.

Wang et al., "Identification of TRP-2 as a Human Tumor Antigen Recognized by Cytotoxic T lymphocytes," *J. Exp. Med.*, 1996, pp. 2207-2216, 184.

Wang et al., "Recognition of an Antigenic Peptide Derived From Tyrosinase-Related Protein-2 by CTL in the Context of HLA-A31 and -A33[1]," *J. Immunol.*, 1998, pp. 890-897, 160(2).

Wang et al., "Selective Histocompatibility Leukocyte Antigen (HLA)-A2 Loss Caused by Aberrant Pre-mRNA Splicing in 624MEL28 Melanoma Cells", *J. Exp. Med.*, 1999, pp. 205-215, 190(2).

Wolfel et al., "A p16[INK4A]-Insensitive CDK4 Mutant Targeted by Cytolytic T Lymphocytes in a Human Melanoma," *Science*, 1995, pp. 1281-1284, 269.

Khong et al., *J Immunother.*, 27(3), 184-190 (2004).

Riley et al., *J. Immunological Methods*, 276, 103-119 (2003).

\* cited by examiner

FIGURE 1

ATGGTGAGAAGCGCTACCCTCATTAAATTTGGTTGTTAGAGGCGCTTCTAAGGAAATTA
AGTCTGTTAGTTGTTTGAATCACATAAAATTGTGTGTGCACGTTCATGTACACATGTGC
ACACATGTAACCTCTGTGATTCTTGTGGGTATTTTTTAAGAAGAAAGGAATAGAAAGC
AAAGAAAATAAAAAATACTGAAAAGAAAAGACTGAAAGAGTAGAAGATAAGGAGAAAA
GTACGACAGAGACAAGGAAAGTAAGAGAGAGAGAGAGCTCTCCCAATTATAAAGCC[ATG]
AGCCCCTTTGGTGGGGGTTTCTGCTCAGTTGCTTGGGCTGCAAAATCCTGCCAGGAGC
CCAGGGTCAGTTCCCCGAGTCTGCATGACGGTGGACAGCCTAGTGAACAAGGAGTGCT
GCCCACGCCTGGGTGCAGAGTCGGCCAATGTCTGTGGCTCTCAGCAAGGCCGGGGGCAG
TGCACAGAGGTGCGAGCCGACACAAGGCCCTGGAGTGGTCCCTACATCCTACGAAACCA
GGATGACCGTGAGCTGTGGCCAAGAAAATTCTTCCACCGGACCTGCAAGTGCACAGGAA
ACTTTGCCGGCTATAATTGTGGAGACTGCAAGTTTGGCTGGACCGGTCCCAACTGCGAG
CGGAAGAAACCACCAGTGATTCGGCAGAACATCCATTCCTTGAGTCCTCAGGAAAGAGA
GCAGTTCTTGGGCGCCTTAGATCTGGCGAAGAAGAGAGTACACCCCGACTACGTGATCA
CCACACAACACTGGCTGGGCCTGCTTGGGCCCAATGGAAGCCAGGCGGAGTTTGGGAAG
TGCAGTGTTTATGATTTTTTTGTGTGGCTCCATTATTATTCTGTTAGAGATACATTATT
AGGACCAGGACGCCCTACAGGGCCATAGATTTCTCACATCAAGGACCTGCATTTGTTA
CCTGGCACCGGTACCATTTGTTGTGTCTGGAAAGAGATCTCCAGCGACTCATTGGCAAT
GAGTCTTTTGCTTTGCCCTACTGGAACTTTGCCACTGGGAGGAACGAGTGTGATGTGTG
TACAGACCAGCTGTTTGGGGCAGCGAGACCAGACGATCCGACTCTGATTAGTCGGAACT
CAAGATTCTCCAGCTGGGAAACTGTCTGTGATAGCTTGGATGACTACAACCACCTGGTC
ACCTTGTGCAATGGAACCTATGAAGGTTTGCTGAGAAGAAATCAAATGGGAAGAAACAG
CATGAAATTGCCAACCTTAAAAGACATACGAGATTGCCTGTCTCTCCAGAAGTTTGACA
ATCCTCCCTTCTTCCAGAACTCTACCTTCAGTTTCAGGAATGCTTTGGAAGGGTTTGAT
AAAGCAGATGGGACTCTGGATTCTCAAGTGATGAGCCTTCATAATTTGGTTCATTCCTT

V

CCTGAACGGGACAAACGCTTTGCCACATTCAGCCGCCAATGATCCCATTTTTGTG (GTG

I   S   N   R   L   L   Y  <u>N   A   T   T   N   I   L   E</u>   H   V   R    K
ATTTCTAATCGTTTGCTTTACAATGCTACAACAAACATCCTTGAACATGTAAG/AAAAG

E   K   A   T   K   E   L   P   S   L   H   V   L (SEQ ID NO: 2)
AGAAAGCGACCAAGGAACTCCCTTCCCTGCATGTGCTG) GTTCTTCATTCCTTTACTGA
TGCCATCTTTGATGAGTGGATGAAAAGATTTAATCCTCCTGCAGATGCCTGGCCTCAGG
AGCTGGCCCCTATTGGTCACAATCGGATGTACAACATGGTTCCTTTCTTCCCTCCAGTG
ACTAATGAAGAACTCTTTTTAACCTCAGACCAACTTGGCTACAGCTATGCCATCGATCT
GCCAGTTTCAGTTGAAGAAACTCCAGGTTGGCCCACAACTCTCTTAGTAGTCATGGGAA
CACTGGTGGCTTTGGTTGGTCTTTTTGTGCTGTTGGCTTTTCTTCAATATAGAAGACTT
CGAAAAGGATATACACCCTAATGGAGACACATTTAAGCAGCAAGAGATACACAGAAGA
AGCC[TAG]GGTGCTCATGCCTTACCTAAGAGAAGAGGCTGGCCAAGCCACAGTTCTGACG
CTGACAATAAAGGAACTAATCCTCACTGTTCCTTCTTGAGTTGAAGATCTTTGACATAG
GTTCTTCTATAGTGATGATGATCTCATTCAGAAGATGCTTAGCTGTAGTTTCCGCTTTG
CTTGCTTGTTTAACAAACCCAACTAAAGTGCTTGAGGCTACCTCTACCTTCAAATAAAG
ATAGACCTGACAATTTGTGATATCTAATAATAACCCCCCCCCAATATTGATTAAGCCT
CCTCCTTTTCTGAAAGCATTTAAAAAAAACAAAAAAAA  (SEQ ID NO. 1)

TRP2 ISOFORM TRP2-6B CONTAINING HLA-A2 RESTRICTED EPITOPES

CROSS-REFERENCE TO RELATED APPLICATIONS

This patent application is the U.S. National Phase of PCT/US02/07698 filed on Mar. 15, 2002, which claims priority to U.S. Provisional Patent Application No. 60/277,108 filed on Mar. 19, 2001.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 16,000 Byte ASCII (Text) file named "223980 2_ST25.txt," created on Apr. 5, 2007.

FIELD OF THE INVENTION

The present invention relates to cancer diagnostics and therapeutics. Specifically, this invention relates to a novel tyrosinase-related protein 2 (TRP2) isoform, TRP2-6b, recognized by cytotoxic T lymphocytes. The present invention further relates to peptides from the TRP2-6b protein. The invention also relates to methods of immunizing mammals with the TRP2-6b protein or peptides to stimulate the production of T cells reactive with the protein or peptides. The invention further relates to methods of detecting, treating, and preventing cancer, preferably melanoma that utilize the TRP2-6b protein and peptides.

BACKGROUND OF THE INVENTION

T cells play an important role in tumor regression in several animal tumor models. Clinical observations have demonstrated that the adoptive transfer of cultured cytotoxic T lymphocytes (CTLs) derived from tumor infiltrating T lymphocytes (TILs) supplemented with interleukin 2 (IL-2) result in tumor regression in 30-40% of patients with metastatic melanoma (Rosenberg et al., N. Engl. J. Med. 319:1676-1680, 1988; Rosenberg et al., JNCI 86:1159-1166, 1995). T cells also play a critical role in the in vivo rejection of melanoma as demonstrated by the presence of T cell infiltrates in regressing tumors after IL-2 based immunotherapy, as well as the association between the clinical response to TIL therapy and the accumulation of injected T cells in tumor sites (Kawakami et al. In: Devita VT, Hellman S, Rosenberg S A, eds. Principle and Practice of Oncology, Update. Philadelphia: Lippincott-Raven, 1997:1-20). In the past decade, immunotherapy and gene therapy utilizing T lymphocytes have emerged as new and promising methods for treating human disease, in particular human cancers. Therefore, identification of antigens recognized by these T cells could provide insight into tumor recognition by autologous T cells, as well as the development of new therapies for cancer patients.

Several studies have demonstrated that specific major histocompatibility complex (MHC)-class I restricted CTL responses are directed against a variety of tumor antigens (Hom et al., J. Immunother. 13:18-30, 1993; Van den Eynde, B. J. and P. van der Bruggen, Curr. Opin. Immunol. 9:684-693, 1997; Rosenberg, S. A., Immunity. 10:281-287, 1999). Based on their pattern of expression, tumor antigens can be grouped into four general categories: 1) tumor-specific shared antigens; 2) tumor-specific mutated antigens; 3) tumor-specific antigens, widely expressed in normal tissues; and 4) melanoma differentiation antigens (MDA).

The first group of tumor-specific shared antigens include cancer-testis antigens such as MAGE and NY-ESO-1. These antigens are expressed on a variety of tumors, including melanoma, but are not expressed in normal tissues except for the testis and placenta (Rosenberg, S. A., Immunity. 10:281-287, 1999; Takahashi et al., Cancer Res. 55:3478-3482, 1995; Chen et al., Proc. Natl. Acad. Sci. U.S.A. 94:1914-1918). The tumor-specific mutated antigens are those antigens which result from mutations and are therefore unique to each patient. These antigens include β-catenin (Robbins et al., J. Exp. Med. 183:1185-1192, 1996), CDK-4 (Wolfel et al., Science. 269:1281-1284, 1995), and MUM-1 (Coulie et al., Proc. Natl. Acad. Sci. U.S.A. 92:7976-7980, 1995). The third group of antigens, although widely expressed in a variety of normal tissues, is selectively expressed on tumors. These antigens include p15 (Robbins et al., J. Immunol. 154:5944-5950, 1995) and PRAME (Ikeda et al., Immunity. 6:199-208, 1997).

The fourth type of tumor antigen includes melanosomal proteins, such as melanoma differentiation antigens (MDA), including MART-1 (Kawakami et al., Proc. Nati. Acad. Sci. U.S.A. 91:3515-3519, 1994; Coulie et al., J. Exp. Med. 180: 35-42, 1994), gp100 (Kawakami et al., Proc. Natl. Acad. Sci. U.S.A. 91:6458-6462), and tyrosinase (Brichard et al., J. EXP. Med. 178:489-495, 1993). Other MDAs which contain antigenic epitopes recognized by specific CTL in the context of HLA-A31 and HLA-A33 (Wang et al., J. Exp. Med. 184: 2207-2216, 1996; Wang et al., J. Immunol. 160:890-897, 1998) include gp75/tyrosinase-related protein 1 (TRP1) Wang et al., J. Exp. Med. 181:799-804, 1995) and tyrosinase-related protein 2 (TRP2) (Wang et al., J. Exp. Med. 184:2207-2216, 1996).

TRP2 is a member of the tyrosinase-related gene family and exhibits approximately 40% amino acid homology to tyrosinase and TRP1. TRP2 is recognized by tumor-reactive CTLs in the mouse (Bloom et al., J. Exp. Med. 185:453-459, 1997) and human (Wang et al., J. Exp. Med. 184:2207-2216, 1996) and HLA-A2 restricted melanoma specific CTL epitopes have been identified in TRP2 using lymphocytes from repeated in vitro stimulation of donor peripheral blood mononuclear cells (PBMC; Parkhurst et al., Cancer Res. 58:4895-4901, 1998; Noppen et al., Int. J. Cancer. 87:241-246, 2000; Sun et al., Int. J. Cancer 87:399-404, 2000; Harada et al., Cancer Res. 61:1089-1094, 2001). Accordingly, the identification of genes encoding other members of the tyrosinase-related gene family and of peptides encoded by these genes, may be important in the treatment and detection of human melanoma and in its treatment and prevention.

SUMMARY OF THE INVENTION

The present invention relates to the identification of a novel tyrosinase-related protein 2 (TRP2), specifically TRP2-6b, a member of the tyrosinase-related gene family. TRP2-6b is identified herewith as a new and potent tumor antigen capable of causing T cells to elicit an immune response.

The present invention therefore relates to nucleic acid sequences that encode the TRP2-6b protein or peptide fragments thereof. The present invention also provides expression vectors comprising the TRP2-6b cDNA or portions thereof alone or in combination with a second DNA sequence encoding at least one co-immunostimulatory molecule. The vectors and host cells may serve as immunogens or vaccines in which expression of TRP2-6b protein or peptide fragments thereof results in the stimulation of antigen specific T lymphocytes in a mammal immunized with the vaccine.

The invention also provides host cells transfected or transduced with a vector comprising DNA encoding TRP2-6b protein or fragments thereof alone or in combination with a second DNA sequence encoding at least one co-immunostimulatory molecule. Such host cells may be useful in adoptive immunotherapy or may serve as vaccines in which expression of the TRP2-6b protein or peptides results in the stimulation of antigen specific T lymphocytes in a mammal immunized with the vaccine.

The present invention also relates to the TRP2-6b protein or peptide fragments thereof, where the protein or peptide fragments may be useful in the detection of cancer or in methods of treating or preventing cancer in mammals.

The present invention also relates to pharmaceutical compositions for the prevention or treatment of mammals afflicted with cancer, where the compositions comprise the TRP2-6b protein or peptide fragments thereof (or nucleic acid sequence encoding the protein or peptide fragment) alone or in combination with one or more co-immunostimulatory molecules and a suitable diluent or carrier.

In yet another embodiment of the instant invention, monoclonal and polyclonal antibodies reactive with the TRP2-6b protein or fragments are provided for use in diagnostic assays.

The invention further relates to a method for treating cancer comprising:
a) immunizing mammals with an amount of TRP2-6b protein or peptide fragments, or nucleic acid sequence encoding said protein or peptide fragments, said amount effective to elicit a specific T cell response;
b) isolating said T cells from said immunized mammals; and
c) administering said T cells to said immunized mammal or to an unimmunized mammal in a therapeutically effective amount.

BRIEF DESCRIPTION OF THE DRAWINGS

FIG. 1 shows a nucleic acid sequence of the novel TRP2-6b gene (SEQ ID NO: 1). The ATG codon of the TRP2 cDNA and the stop codon TAG are boxed. The additional 99 base pair sequence encoded by the novel TRP2-6b gene is enclosed by parentheses, where exons 6b and 6c are separated by a slash and the nucleotide sequence encoding for exons 6b and 6c are translated in the corresponding amino acid sequence (SEQ ID NO: 2)using the single letter amino acid code. The epitope recognized by TIL clone MB4 is underlined.

DETAILED DESCRIPTION OF THE INVENTION

Figure 2:
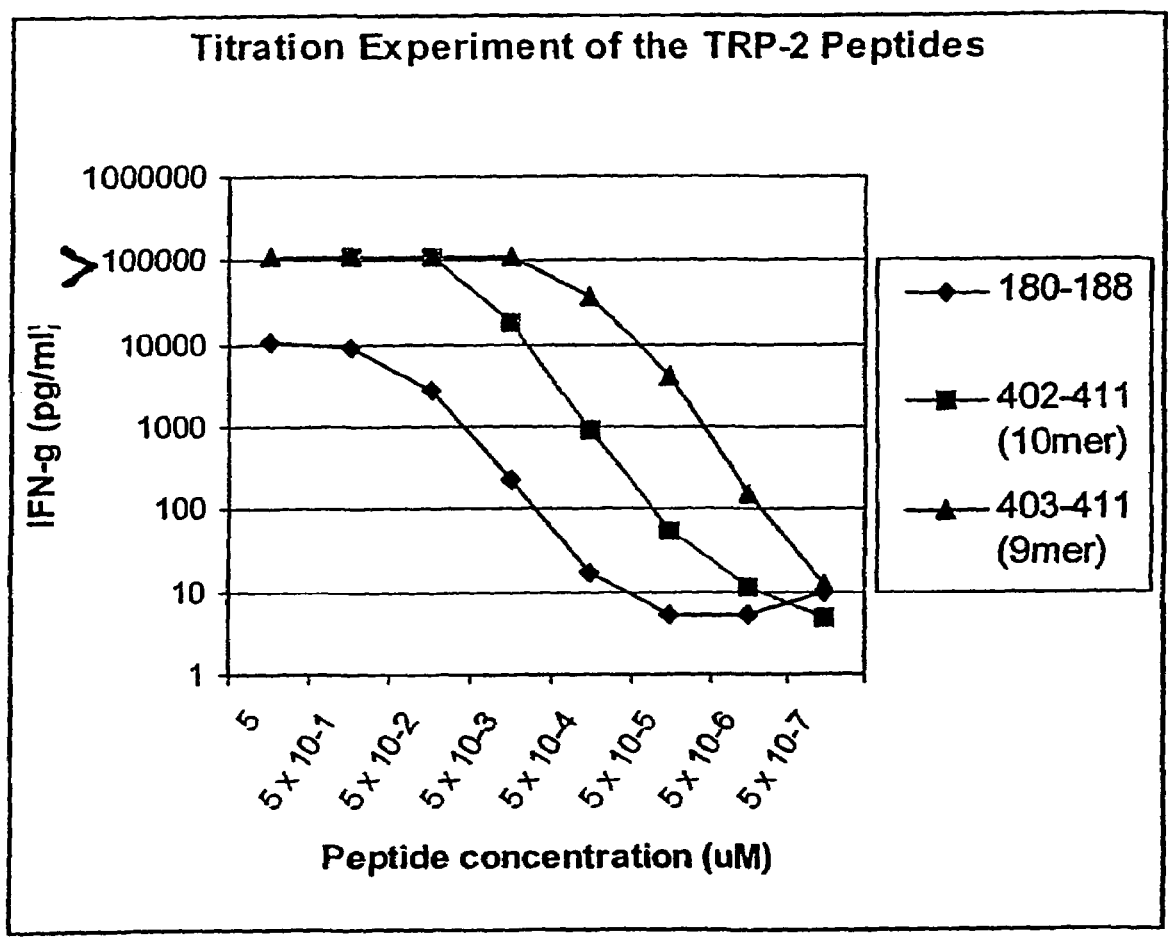
FIG. 2 shows IFN-γ release by TIL clone MB4 co-cultured with T2 cells pulsed with decreasing concentration of peptides TRP2-6b:402-411 and TRP2-6b:403-411.

The present invention relates to a novel tumor antigen, the TRP2-6b protein expressed primarily in melanomas. Elevated levels of expression of TRP2-6b have been demonstrated in both normal and cancerous cell lines and the TRP2-6b protein and peptides are immunologically recognized by T lymphocytes of the immune system.

The TRP2-6b DNA is identical to the previously identified TRP2 cDNA of Wang et al., (*J. Exp. Med.* 184:2207-2216, 1996) with the exception of a 99 nucleotide insert between exon 6 and exon 7 of the TRP2 gene (FIG. 1). The additional insert is composed of two separate sequences named 6b and 6c. Each has complete homology with two noncontiguous sequences in intron 6 of the TRP2 gene.

The present invention therefore relates to nucleic acid sequence encoding TRP2-6b protein or TRP2-6b peptides. Due to the degeneracy of the genetic code, it is to be understood that several choices of nucleotides may be made that will lead to a sequence capable of directing production of the TRP2-6b protein or peptides thereof. Therefore, nucleic acid sequences that are functionally equivalent to the sequences described herein are intended to be encompassed within the present invention. One such nucleic acid sequence encoding the TRP2-6b protein is disclosed herein as SEQ ID NO:1.

The present invention also relates to expression vectors comprising the nucleic acid sequences of the invention where such vectors are any expression vectors which can carry and express the nucleic acid sequences encoding the TRP2-6b protein or peptides in prokaryotic or eukaryotic host cells. Such vectors include, but are not limited to, vaccinia, adenovirus, and the like.

Further, the invention also encompasses host cells transformed, transfected, or infected with the vector expressing the TRP2-6b proteins or peptides. The host cell can endogenously express an appropriate HLA-restricted molecule, or may be recombinantly engineered to express an exogenous HLA-restricted molecule, using methods known in the art, wherein the preferred HLA-restricted molecule is HLA-A2-restricted. Such host cells include, but are not limited to, T cells.

TRP2-6b encodes a protein identical to that of previously identified TRP2 of Wang et al., (*J. Exp. Med.* 184:2207-2216, 1996) except for an in-frame insert of a 33 amino acid sequence (SEQ ID NO: 2) introduced after amino acid 393of the TRP2 protein. The present invention therefore relates to the TRP2-6b protein having the sequence shown in SEQ ID NO:5. The TRP2-6b protein having the 552 amino acid sequence shown in SEQ ID NO: 5, forms part of, or is derived from, cancers including but not limited to primary or metastatic melanoma and the like.

The term "melanoma" includes, but is not limited to melanomas, metastatic melanomas, melanomas derived from either melanocytes or melanocyte related nevus cells, melanocarcinomas, melanoepitheliomas, melanosarcomas, melanoma in situ, superficial spreading melanoma, nodular melanoma, lentigo, maligna melanoma, acral lentiginous melanoma, invasive melanoma or familial atypical mole and melanoma (FAM-M) syndrome.

The present invention also relates to peptides from the TRP2-6b protein where the peptide consists of at least 9 contiguous amino acids from the novel TRP2-6b protein, preferably 9-15 contiguous amino acids, more preferably 9-11 contiguous amino acids.

In a preferred embodiment, the isolated peptide comprises 9 contiguous amino acids selected from between amino acids 394 to 427 of the TRP2-6b protein, and preferably, the peptide of the present invention comprises TRP2-6b:402-411 or TRP2-6b:403-411 having the amino acid sequences NATT-NILEHV (SEQ ID NO:3) or ATTNILEHV (SEQ ID NO:4), respectively.

The present invention also encompasses peptides having sufficient homology to TRP2-6b peptides such as to effectively elicit a T cell response.

Preferred peptides are those having sufficient homology to TRP2-6b peptides selected from between amino acids 394-427 of the TRP2-6b protein. Such peptides may have conservative amino acid changes at one or more positions, preferably substitutions at no more than 3 positions, more preferably substitutions at no more than 2 positions, and most preferably substitutions at no more than 1 position. By conservative amino acid changes is meant, an amino acid change at a particular position which is the same type as originally presented; i.e. a hydrophobic amino acid exchanged for a hydrophobic amino acid, a basic amino acid for a basic amino acid, etc. Such amino acid changes do not significantly alter the overall charge and configuration of the peptide and therefore such variants maintain the anti-cancer activity of a peptide. Examples of such conservative changes are well known to those skilled in the art and are within the scope of the present invention. Conservative substitutions include, for example, the substitution of one non-polar (hydrophobic) residue such as isoleucine, valine, leucine, cysteine, or methionine for another, the substitution of one polar (hydrophilic) residue for another such as between arginine and lysine, between glutamine and asparagine, between glycine and serine, between alanine and threonine, the substitution of one basic residue such as lysine, arginine, or histidine for another, or the substitution of one acidic residue, such as aspartic acid or glutamic acid.

The TRP2-6b peptides also include peptide conjugates, chimeric proteins, fusion proteins, and peptide nucleic acids. For example, multi-epitope conjugates comprising multiple copies of one or more T cell epitopes can be used to increase the peptide specific T cell responses, thereby lowering the dosage of priming antigen necessary. The peptides of this invention may also be modified to enhance their binding to MHC molecules and immunogenicity.

The TRP2-6b protein and peptides thereof may be purified and isolated from natural sources such as from primary clinical isolates, cell lines, and the like. The TRP2-6b protein and peptides may also be obtained by chemical synthesis or by recombinant DNA techniques well known in the art. Techniques for chemical synthesis are described in Steward et al. ("Solid Phase Peptide Synthesis", W. H. Freeman & Co., San Francisco, 1969); Bodansky et al. ("Peptide Synthesis", John Wiley & Sons, Second Edition, 1976); Meienhofer ("Hormonal Proteins and Peptides" Vol. 2, P. 46, Academic Press, New York, 1983); and Schroder et al. ("The Peptides" Vol. 1, Academic Press, New York, 1965).

Of particular interest are peptides of TRP2-6b recognized by autologous CTL in patients with cancer, in particular, melanoma. Of further interest are peptides derivatives thereof recognized by major histocompatibility complex (MHC)-restricted CTL, in particular MHC class I restricted CTLs where MHC is a generic designation encompassing the histocompatibility antigen systems described in different species including the human leukocyte antigens (HLA). A preferred HLA subtype recognized by the peptides of this invention are the HLA-A2 subtype, more preferably the HLA-A0201 class.

The present invention therefore also relates to a method of detecting the presence of cancer, preferably melanoma, or a precancer, in mammals, preferably humans. In one embodiment, the method comprising contacting cytotoxic T lymphocytes from the mammal with the TRP2-6b protein, or peptides thereof and measuring the reactivity of said T lymphocytes with said protein or peptide.

In another embodiment, a sample obtained from a mammal suspected of having melanoma is directly analyzed for the presence of TRP2-6b nucleic acid sequence or encoded protein by contacting said sample with TRP2-6b nucleic acid sequence (or fragments thereof) or with antibodies to the TRP2-6b protein or peptides.

The TRP2-6b protein is further useful in methods of preventing or treating cancer, or precancer in a mammal, preferably human. The TRP2-6b protein, peptides, or variants thereof may be in the form of a derivative in which other constituents are attached thereto such as radioactive labels, biotin, and fluorescein. A targeting agent may also be used to allow for specific targeting to a specific organ, tumor or cells types. Such targeting agents may be hormones, cytokines, cellular receptors and the like. The TRP2-6b protein of the present invention may be prepared in the form of a kit, alone or in combination with other reagents.

The present invention therefore relates to pharmaceutical compositions in which the TRP2-6b protein or peptides may be formulated with pharmaceutically acceptable carriers by methods known in the art. The composition is useful as a vaccine to prevent or treat cancer. The composition may further comprise at least one co-immunostimulatory molecule. Co-immunostimulatory molecules to be used in conjunction with the TRP2-6b protein or peptide of the present invention for stimulating antigen specific T cell responses include but are not limited to one or more major histocompatability complex (MHC) molecules, such as class I and class II, preferably a class I molecule.

As the TRP2-6b protein or peptides are useful in inducing a tumor-specific cell mediated immunity against melanoma, the TRP2-6b protein or peptides are useful in methods of preventing or inhibiting cancer. In one embodiment, patients are directly immunized in an attempt to boost immune responses against the tumor. In such active immunotherapy, the immunogen can be the TRP2-6b protein or peptides or nucleic acid molecules encoding said protein or peptides.

For DNA-based immunizations, the insertion of a gene encoding TRP2-6b protein or peptides into high efficiency expression systems, such as E. coli, yeast, baculovirus, or vaccinia virus and the like provides the opportunity to obtain large amounts of purified tumor antigen, i.e. TRP2-6b for use in immunization.

The injection of "naked" DNA directly into muscle or into the skin has recently been utilized and shown to raise both cellular and humoral immune reactions to encoded antigens (Cooney, et al., *Lancet* 337:567, 1991; Wolff et al., *Science* 247:1465, 1990; Davis et al., *Hum. Gene Ther.* 4:151, 1993; Yang, 1990; Williams et al., *Proc. Natl. Acad. Sci. USA* 88:2726, 1991; Fynan et al., *Proc. Natl. Acad. Sci. USA* 90:11478, 1995; Eisenbraum et al., *DNA and Cell Bio.* 12:791, 1993; Fuller, et al., *AIDS Res. Hum. Retrovir.* 10:1433, 1994; Acsadi et al., *Nature*, 352:815, 1991). Techniques using non-viable DNA vectors have the advantage of ease of preparation and safety of administration. The alternative nucleic acid sequence of the present invention is therefore useful as an immunogen and as a DNA vaccine against cancer. The DNA sequences encoding the TRP2-6b proteins or peptides of the present invention may be administered using a gene gun in amounts to elicit a cellular response against a cancer cell. Nanogram quantities are useful for such purposes.

An effective form of immunization involves the incorporation of genes encoding immunogenic molecules into recombinant bacteria such as BCG, Salmonella, or Listeria or into recombinant viruses such as vaccina, fowlpox, or adenovirus and the like. The genes encoding antigens can be expressed either alone or in combination with genes encoding co-immunostimulatory molecules or other genes which can stimulate the immune response following infection. Studies with model tumor antigens in murine models have demonstrated that incorporation of the gene for IL-2 can increase the immunogenicity of tumor antigens and even mediate the regression of established lung metastases bearing these antigens and even mediate the regression of established lung metastases bearing these antigens. Active immunotherapy followed by the exogenous administration of co-immunostimulatory cytokines such as IL-2, IL-6, IL-10, etc. may also be used to improve immune responses.

Alternatively, the immunodominant peptides from the TRP2-6b could readily be synthesized in vitro and purified in large amounts for immunizaton alone or in a form intended to improve their immunogenicity such as in combination with an adjuvant, linkage to lipids/liposomes or helper peptides, or pulsed onto antigen presenting cells. Modification of individual amino acids of the immunodominant peptides to improve binding efficiency to MHC antigens can potentially increase immunogenicity compared to the native peptide.

The present invention therefore relates to methods of preventing or inhibiting cancer, preferably melanoma in mammals, by administering TRP2-6b protein or peptides (or nucleic acid sequences encoding them) to the mammal via routes of administration that include, but are not limited to intravenous, intramuscular, subcutaneous, intradermal, intraperitoneal, intrathecal, intraplerural, intrauterine, rectal, vaginal, topical, intratumor and the like.

Administration may also be by transmucosal or transdermal means. For transmucosal or transdermal administration penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be by nasal sprays, for example, or suppositories. For oral administration, the TRP2-6b protein, peptides, or variants thereof are formulated into conventional oral administration forms such as capsules, tablets, and toxics.

Generally, it is desirable to provide the recipient with a dosage of TRP2-6b protein or peptide of at least about 1 pg/kg body weight, preferably at least 1 ng/kg body weight, more preferably at least about 1 µg/kg body weight or greater of the recipient. A range of from about 1 ng/kg body weight to about 100 mg/kg body weight is preferred although a lower or higher dose may be administered. The dose is effective to prime, stimulate, and/or cause the clonal expansion of antigen specific T lymphocytes, preferably cytotoxic T lymphocytes, which in turn are capable of preventing or inhibiting cancer in the recipient, preferably human.

In another embodiment, passive immunotherapy with genetically modified immune cells (commonly referred to as adoptive immunotherapy) capable of recognizing human tumor antigens is effective in mediating the regression of cancer in selected patients with metastatic melanoma. In vitro techniques have been developed in which human lymphocytes are sensitized in vitro to tumor antigen immunodominant peptides presented on antigen presenting cells. By repetitive in vitro stimulation, cells can be derived with a far greater capacity to recognize human tumor antigens than the TIL that were used to clone the gene encoding the TRP2-6b proteins. Thus by repeated in vitro stimulation with the TRP2-6b protein or peptides of the present invention, lymphocytes could be derived with 50 to 100 times more potency of TIL. The adoptive transfer of these cells may be more effective in mediating a tumor regression in vivo that are conventionally grown TIL.

The present invention therefore includes a method for treating cancer, preferably melanoma, comprising:
a) immunizing mammals with an amount of TRP2-6b protein or peptides, or an expression vector capable of directing host organism synthesis of said protein or peptides, in an amount effective to elicit a specific T cell response to the protein or peptide;
b) isolating said T cells from said immunized mammal; and
c) administering said T cells to said immunized mammal or to an unimmunized mammal in a therapeutically effective amount.

T cell populations reactive against the TRP2-6b protein or peptide may also be isolated from a peripheral blood sample of a donor immunized with the TRP2-6b protein or peptides from about 3 to 30 days after immunization. For example, Epstein-Barr virus (EBV) can be used to immortalize human lymphocytes or a human fusion partner can be used to produce human-human hybridomas. Primary in vitro immunization with the TRP2-6b protein or peptide can also be used tin the generation of T cells reactive to the immunogenic peptide.

T cells are cultured for about 7 to about 90 days (Yanelli, J. R., *J. Immunol. Methods* 139:1-16, 1991) and subsequently screened to determine the clones having the desired reactivity against the TRP2-6b protein or peptide using known methods of assaying T cell reactivity; T cells producing the desired reactivity are thus selected.

The previously described T cells may also be used in vivo for the treatment of individuals afflicted with cancer by administering from about $10^7$ to $10^{11}$ T cells to a mammal intravenously, intraperitoneally, intramuscularly, or subcutaneously. Preferred routes of administration are intravenously or intraperitoneally.

The present invention also relates to polyclonal, monoclonal, and recombinant antibodies elicited by and immunoreactive with, the TRP2-6b peptide having at least 9 contiguous amino acids and comprising the amino acid sequence as in SEQ ID NO:3 or SEQ ID NO:4, and analogs thereof for use as a diagnostic and/or therapeutic reagent.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

EXAMPLES

Example 1

Materials and Methods

Patient MM

Patient MM is a 63 year old female who underwent a wide local excision of a primary melanoma on her back in 1981. In May 1997, she developed a subcutaneous metastasis on her left chest wall, which was resected, and she was started on a chemoimmunotherapy regimen consisting of cisplatin, vinblastine, dacarbazine, IL-2, and IFN-α. In June of 1998, the patient had developed metastatic disease in multiple sites including the lungs, liver, intrapelvic area, left abdominal wall, and left thigh. She was started on a 4-peptide vaccination protocol using 1 mg each of gp100:209-217 (210M), gp100:280-288 (288V), MART-1:27-35, and tyrosinase:368-376 in IFA subcutaneously every three weeks. Most of the tumor completely regressed after 2 cycles of treatment, including complete resolution of a large tumor in her left thigh, in intrapelvic mass, a liver lesion, and most of the nodules in her lungs. She completed a total of 6 cycles of vaccinations in October 1998. In October 1999, she developed a frontal lobe metastatic brain lesion, and a subcutaneous nodule on her right chest wall, both of which were resected. Bulk TIL 1790 used in this study was grown from the chest wall lesion. In March 2000, she underwent a second right temporal craniotomy for resection of recurrent disease at the prior resection site, followed by whole brain irradiation. The patient is doing well at this time, with disease limited to three small lung lesions (~1×1 cm) that are growing slowly.

Cell Lines

Melanoma-reactive CTL were derived from bulk tumor infiltrating lymphocyte (TIL) cultures grown in Iscove's Modified Dulbecco's Medium (IMDM) (Gibco BRL; Gaithersburg, Md.) containing 6000 IU/ml of human recombinant IL-2 (Chiron; Emeryville, Calif.) as previously described (Topalian, et al., *J. Immunol. Methods*. 102:127-141, 1987). CTL clones were derived from bulk TIL cultures by limiting dilution with the addition of anti-CD3 antibody (OKT-3; Ortho Pharmaceuticals; Raritan, N.J.). Briefly, 5×10$^4$ irradiated (3000-3400 cG) allogeneic PBMC from three different donors were plated in round-bottom 96-well plates with 0.5 to 90 T cells per well. Cells were cultured in RPMI 1640 medium (Gibco BRL) containing 20% heat inactivated fetal bovine serum (FBS) (Gibco BRL) and 30 ng/ml OKT-3 antibody with 300 IU/ml IL-2. The same dose of IL-2 was added on day 7, and clones were tested for specific anti-tumor activity 14 days after stimulation. After testing, the remainder of T cells were expanded by plating them in a T25 flask with 2.5×10$^7$ irradiated allogeneic PBMC from three different donors in 25 ml RPMI 1640 medium containing 10% FBS and 30 ng/ml OKT-3 antibody. Subsequent expansion was similarly done, but with 1-2 million CTL and 2.5×10$^8$ allogeneic PBMC plated in an upright T162 flask in 150 ml medium.

The melanoma cell lines 624-28, 624-38, 938, 526, 888, 888A2, F002S, and F002R were established in the Surgery Branch (NCI). 624-28 and 624-38 were derived from the same parental cell line 624-mel and share a similar pattern of antigen and HLA allele expression except for HLA-A0201, which was expressed in 624-38, but not in 624-28 because of aberrant pre-mRNA splicing (Wang et al, *J. Expt. Med.* 190: 205-215, 1999). 888-A2-mel was obtained by stable transfection of 888-mel with HLA-A2 cDNA (pcDNA3 plasmid; Invitrogen). F002S is deficient in gp100 expression. F002R was derived from F002S by in vitro immunoselection for loss of MART-1 expression. T2 cells, deficient in transporter associated protein, are used to test HLA-A2-restricted peptides for CTL activity. The 293 cell line was derived from primary human embryonal kidney cells and is used for transfection purpose. The 293A2 cell line was obtained by stable transfection of 293 cells with the HLA-A2 gene. All cell lines were maintained in RPMI 1640 supplemented with 10% heat-inactivated FBS, 10 mM HEPES buffer, 100 U/ml penicillin-streptomycin (Biofluids), and 2 mM L-glutamine (Biofluids). This medium is referred to as complete medium (CM).

cDNA Library Screening

The 624-mel cDNA expression library prepared by Dr. Rong-Fu Wang (Baylor College of Medicine) was used. Briefly, total RNA was extracted from 624-mel using Trizol® reagent (Life Technologies). Poly(A) RNA was purified from total RNA by the poly(A) tract isolation system (Promega; Madison, Wis.) and converted to cDNA using an oligo(dT) primer. The cDNA was ligated to BstXl adaptors and digested with Notl, then ligated to the expression vector pEAK8. The cDNA was electroporated into DH10B cells (Life Technologies). Pools containing~100 cDNA clones were prepared from bacteria. The plasmid DNA (200 ng) was transfected into 293A2 cells with Effectene reagent™ (Qiagen; Valencia, Calif.). Briefly, 4×10$^4$ cells per well were plated in flat-bottom 96 well plates in CM the day before transfection. On the day of transfection, plasmid DNA (200 ng) from each pool was diluted in 29 µl Buffer EC. Next, 0.8 (µl Enhancer was added and mixed. The mixture was incubated at room temperature for 5 minutes. After the incubation, 5 µl of Effectene™ reagent was diluted in 17.5 µl Buffer EC and then added to and mixed with the DNA-Enhancer mixture. The mixture was incubated for 10 minutes at room temperature. During incubation, the expended media from 293A2 plates were removed and replaced with 100 µl fresh CM. After incubation, the DNA-Enhancer-Effectene™ mixture was added drop-wise onto the cells. The plates were then incubated at 37° C./5% CO$_2$ for 24 hours. The following day, the expended media were removed and replaced with 100 µl fresh CM. A total of 5×10$^4$ CTL in 100 µl CM were added to each well, and the plates were incubated at 37° C. for 24 hours. After the incubation, the plates were centrifuged at 1500 rpm for 5 minutes, and the supernatants were harvested for IFN-γ detection in an ELISA assay.

DNA Sequencing

Sequencing of the isolated cDNA clone was performed with an ABI Prism™ 310 automated capillary electrophoresis instrument (Perkin-Elmer; Foster City, Calif.) using the Dye™ Terminator Cycle Sequencing Ready Reaction 5 kit (Perkin-Elmer). Searches for sequence homology were done with the GenBank database using the BLAST algorithm (S. F. Altschul, et al., *Nuc. Acids Res.*, 25:3389-4302 (1997)).

Peptide Synthesis

Peptides were synthesized using a solid phase method based on standard Fmoc chemistry on a multiple peptide synthesizer (Gilson Co.; Worthington, Ohio). Peptide identity was verified by laser desorption mass spectrometry (Bio-Synthesis, Inc.; Lewisville, Tex.). Lyophylized peptides were solubilized in DMSO at 10 mg/ml concentration.

Example 2

Characterization of TIL1790 Which Recognizes a Melanoma Antigen

The 1790 TIL line was isolated from a metastatic subcutaneous lesion in the right chest wall of patient MM, who was typed as HLA-A2 and HLA-A3. The 1790 TIL line recognized a panel of melanoma cell lines matched for HLA-A2, but did not recognize non-HLA-A2 cell lines (TABLE 1). Additionally, TIL 1790 was tested against peptide-pulsed T2 cells, and was found to recognize MART-1 (27-35), but not the tyrosinase or two gp100 peptides she was initially immunized against. Surprisingly, TIL 1790 recognized both MART-1 peptide and F002R, a melanoma cell line that does not express MART-1. The lack of MART-1 expression on F002R was simultaneously confirmed by the lack of F002R recognition by a control anti-MART-1 CTL clone (clone V2C8). Therefore, the 1790 TIL line recognized at least one other melanoma antigen other than MART-1.

TABLE 1

Specific activity of TIL 1790

| TARGET | HLA-A2 | IFN-g (pg/ml) |
|---|---|---|
| 526 | + | >1000 |
| 624-38 | + | >1000 |
| 888A2 | + | 884 |
| 697 | + | 69 |
| 1102 | + | 361 |
| F002R | + | >1000 |
| F002S | + | >1000 |
| 293A2 | + | 22 |
| 938 | − | 4 |
| 624-28 | − | 18 |
| 888 | − | 3 |
| T2 alone | + | 22 |
| T2-gp154 | + | 47 |
| T2-gp209 | + | 56 |
| T2-gp280 | + | 40 |
| T2-MART-1 | + | >1000 |
| T2-Tyrosinase | + | 26 |

$2 \times 10^4$ T cells were incubated with $1 \times 10^5$ targets for 24 h, and the release of IFN-g (pg/ml) was measured in an ELISA assay.

Example 3

Identification of the Melanoma Antigen of TIL 1790

In order to identify the antigen(s) recognized by TIL 1790, several CTL clones were generated from said TIL line by limiting dilution. CTL clones MR7, MB4, and M8 were selected for further analysis due to their ability to specifically release cytokine, IFN-γ, in response to HLA-A2 melanoma cell lines, but not to cell lines which did not express HLA-A2 (TABLE 2). Additionally, these clones were selected because they did not recognize T2 cells pulsed with peptides from MART-1, gp-100, and tyrosinase. Since non-HLA-A2 melanoma cell lines, such as 888mel, stimulated cytokine release from clones MR7 and MB4 after being stably transfected with HLA-A2, these clones therefore expressed the antigen(s) of interest, and further, the MR7 and MB4 clones recognized a melanoma antigen restricted by HLA-A2. Clone M8 did not recognize 888mel or 888A2; however, did react with 624-38, but not the HLA-A2 negative variant, 624-28. These results suggested that M8 also recognized an HLA-A2-restricted melanoma antigen. Confirmation of HLA-A2-restriction was confirmed by antibody blocking studies performed only on clone MR7. Clones MR7, M8, and MB4 were further tested for recognition of previously identified antigens in a co-culture assay using 293A2 cells transfected with cDNA encoding antigens (TABLE 3). Clone MR7 recognized TRP2, clone M8 recognized NY-ESO, and clone MB4 did not recognize any of the known antigens tested. Additionally, a cDNA clone coding for TRP2 was simultaneously isolated and sequenced when CTL clone MR7 was used for screening the 624 melanoma library. TABLE 4 shows the epitopes recognized by CTL MR7 and CTL M8, including TRP2:180-188, and the overlapping NY-ESO peptides, NY-ESO: 157-167, NY-ESO:157-165, and NY-ESO:155-163.

TABLE 2

Recognition of melanoma cell lines by TIL clones MR7, MB4, and M8

| Stimulator Cell Line | HLA-A2 | Exp. 1 MR7 | Exp. 2 MB4 | M8 |
|---|---|---|---|---|
| | | | FN-g (pg/ml) | |
| 624-38 | + | >1000 | >1000 | >1000 |
| 526 | + | >1000 | >1000 | 81 |
| 888A2 | + | 206 | 196 | 101 |
| F002S | + | >1000 | >1000 | >1000 |
| F002R | + | >1000 | 260 | 834 |
| 1760 | + | 516 | 456 | >1000 |
| 624-28 | − | 57 | 26 | 83 |
| 938 | − | 50 | 62 | 95 |
| 888 | − | 43 | 47 | 101 |
| None | | 40 | 59 | 152 |

$5 \times 10^4$ T cells were incubated with $1 \times 10^5$ target cells for 24 h, and the release of IFN-g (pg/ml) was measured in an ELISA assay.

TABLE 3

Recognition of gene transfectants by TIL clones MR7, MB4, and M8

| Transfected gene | Exp. 1 MR7 | Exp. 2 MB4 | M8 |
|---|---|---|---|
| | | FN-g (pg/ml) | |
| gp100 | 8 | 94 | 0 |
| MART-1 | 4 | 92 | 0 |
| TYR | 9 | 87 | 0 |
| TRP-1 | 5 | 44 | 0 |
| TRP-2 | >1000 | 114 | 0 |
| MAGE-1 | 5 | 67 | 0 |
| MAGE-3 | 0 | 109 | 0 |
| AIM | 7 | 53 | 0 |
| NY-ESO | 5 | 91 | >1000 |

Cytokine release (pg/ml) following coincubation of T cells with 293A2 cells transfected with cDNA encoding known antigens for 24 h was measured using an IFN-g ELISA (Background activity from 293 transfectants has been subtracted).

TABLE 4

Peptide recognition of TIL clones MR7 (A) and M8 (B)

| | Target | IFN-g (pg/ml) |
|---|---|---|
| A) | T2-MART-1 | 41 |
| | T2-TRP-2: 180-188 | >1000 |
| | T2-TRP-2: 455-463 | 10 |
| | None | 0 |
| B) | T2-NY-ESO: 155-163 | 407 |
| | T2-NY-ESO: 157-165 | >1000 |
| | T2-NY-ESO: 157-167 | >1000 |
| | T2-gp154 | 32 |

Example 4

Isolation of a cDNA Clone

A cDNA library prepared from 624mel was used to screen for a gene encoding reactivity with CTL MB4. Plasmid DNA from pools containing approximately 100 cDNA clones was transiently transfected into 293A2 cells, a human embryonal kidney cell line transfected with the gene encoding HLA-A2. The cDNA in one of 400 pools strongly stimulated IFN-γ release from CTL MB4. The positive cDNA clone (cDNA 198) which induced a high level of IFN-γ secretion from TIL clone MB4 (Table 5) was identified upon subcloning.

TABLE 5

Stimulation of TIL clone MB4 by 293A2 cells transfected with cDNA 198

| Stimulator | IFN-g (pg/ml) |
|---|---|
| 293A2 + cDNA 198 | >1000 |
| 293 + cDNA 198 | 2 |
| 293A2 + GFP | 8 |
| 293 + GFP | 9 |
| 293A2 | 0 |
| 293 | 2 |

293 cells transfected with cDNA 198 or GFP, and 293A2 cells transfected with GFP were used as control.

Example 5

Sequence Determination of the Positive Clone

The sequence of the cDNA 198 clone was determined to be identical to that of the TRP2 gene with the exception of a 99 nucleotide insert between exon 6 and exon 7 of the TRP2 gene (FIG. 1). The additional insert was composed of two distinct and separate sequences, named 6b and 6c, where each showed complete homology with two non-contiguous sequences in intron 6 of the TRP2 gene. The deduced amino acid sequence was translated in-frame with the TRP2 product. The two polypeptides encoded by cDNA 198 and the cDNA encoding the previously described TRP2 were identical except for an in frame insert of 33 amino acid sequence, following amino acid 393. Since both 6b and 6c were coding sequences, and their flanking regions conformed to the intron consensus motif GT-AG, 6b and 6c were thus identified as novel exons, alternatively spliced from intron 6 of the TRP2 gene. Additionally, the insertion in the coding region, the sequence of cDNA 198 also differed from TRP2 in the non-coding regions. The initial 122 base pairs of 414 base pairs of the 5' untranslated region (5'UTR) of TRP2 was deleted in cDNA 198. However, the 3' UTR of TRP2 was further extended with a 10-base pair sequence in cDNA 198. The protein encoded by cDNA 198 was accordingly named TRP2-6b.

Example 6

Identification of the T Cell Epitope in TRP2-6b

Figure 3:
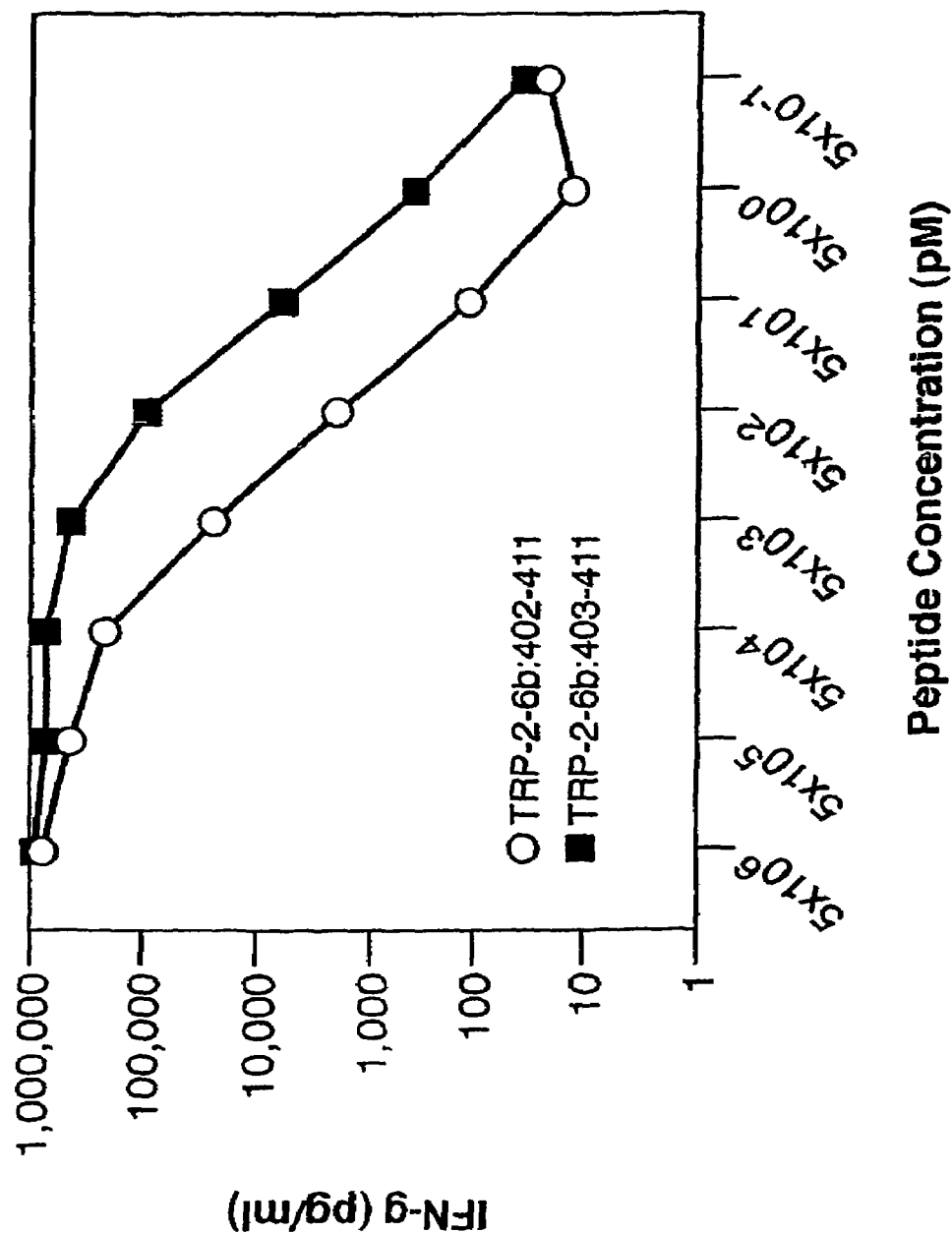
FIG. 3 shows IFN-γ release by TIL clone MB4 co-cultured with T2 cells pulsed with decreasing concentration of peptides TRP2-6b:402-411, TRP2-6b:403-411, and TRP2:180-188.

CTL MB4 did not recognize 293A2 cells transfected with TRP2 cDNA and thus, suggested that the antigenic epitope may be encoded by the 99 base pair sequence of the new exons 6b and 6c. A peptide-HLA motif search program was used to generate 22 possible peptides predicted to bind HLA-A2 from the novel 33 amino acid sequence encoded by exons 6b and 6c and 10 amino acids upstream and downstream. These peptides were pulsed on T2 cells and tested for recognition by CTL MB4. Two peptides in particular, ATT-NILEHV (SEQ ID NO: 4) and NATTNILEHV (SEQ ID NO: 3), designated TRP2-6b:403-411 and TRP2-6b:402-411, respectively, were recognized by CTL MB4 when pulsed on T2 cells (TABLE 6). The decapeptide TRP2-6b:402-411 sensitized target cells for recognition by CTL MB4 at 500 pg/ml, whereas the nonapeptide TRP2-6b:403-411 was recognized at a concentration of 5 pg/ml (FIG. 2). Further, FIG. 3 shows INF-γ release by TIL clone MB4 co-cultured with T2 cells pulsed with decreasing concentration of peptides TRP2-6b: 402-411, TRP2-6b:403-411, and TRP2:180-188.

TABLE 6

Candidate HLA-A2-restricted peptides from TRP-2-6b and their recognition by CTL MB4 as measured by IFN-g release

| Peptide | Sequence | IFN-g (pg/ml) | |
|---|---|---|---|
| 9mer: | | | |
| 399-407 | LLYNATTNI | 6 | (SEQ ID NO: 6) |
| 427-435 | VLHSFTDAI | 4 | (SEQ ID NO: 7) |
| 386-394 | AANDPIFVV | 7 | (SEQ ID NO: 8) |
| 385-393 | SAANDPIFV | 8 | (SEQ ID NO: 9) |
| 419-427 | ELPSLHVLV | 6 | (SEQ ID NO: 10) |
| 426-434 | LVLHSFTDA | 5 | (SEQ ID NO: 11) |
| 418-426 | KELPSLHVL | 6 | (SEQ ID NO: 12) |
| 415-423 | KATKELPSL | 3 | (SEQ ID NO: 13) |
| 392-400 | FVVISNRLL | 6 | (SEQ ID NO: 14) |
| 403-411 | ATTNILEHV | >1000 | (SEQ ID NO: 4) |
| 424-432 | HVLVLHSFT | 6 | (SEQ ID NO: 15) |
| 10mer: | | | |
| 399-408 | LLYNATTNIL | 10 | (SEQ ID NO: 16) |
| 398-407 | RLLYNATTNI | 5 | (SEQ ID NO: 17) |
| 418-427 | KELPSLHVLV | 5 | (SEQ ID NO: 18) |
| 425-434 | VLVLHSFTDA | 4 | (SEQ ID NO: 19) |
| 426-435 | LVLHSFTDAI | 6 | (SEQ ID NO: 20) |
| 385-394 | SAANDPIFVV | 4 | (SEQ ID NO: 21) |
| 394-403 | VISNRLLYNA | 41 | (SEQ ID NO: 22) |
| 419-428 | ELPSLHVLVL | 2 | (SEQ ID NO: 23) |
| 402-411 | NATTNILEHV | >1000 | (SEQ ID NO: 3) |
| 390-399 | PIFVVISNRL | 2 | (SEQ ID NO: 24) |
| 416-425 | ATKELPSLHV | 4 | (SEQ ID NO: 25) |

Using an HLA peptide motif search program, 22 peptides with predicted HLA-A2 binding were made from the new 33-amino acid sequence as well as 10 amino acids upstream and downstream of the sequence. 5 × 10⁴ TIL clone MB4 cells were incubated with 1 × 10⁵ peptide-pulsed T2 cells (1 uM, pulsed for 2 h) for 24 h, and IFN-g release was measured in an ELISA assay.

Example 7

Figure 4:
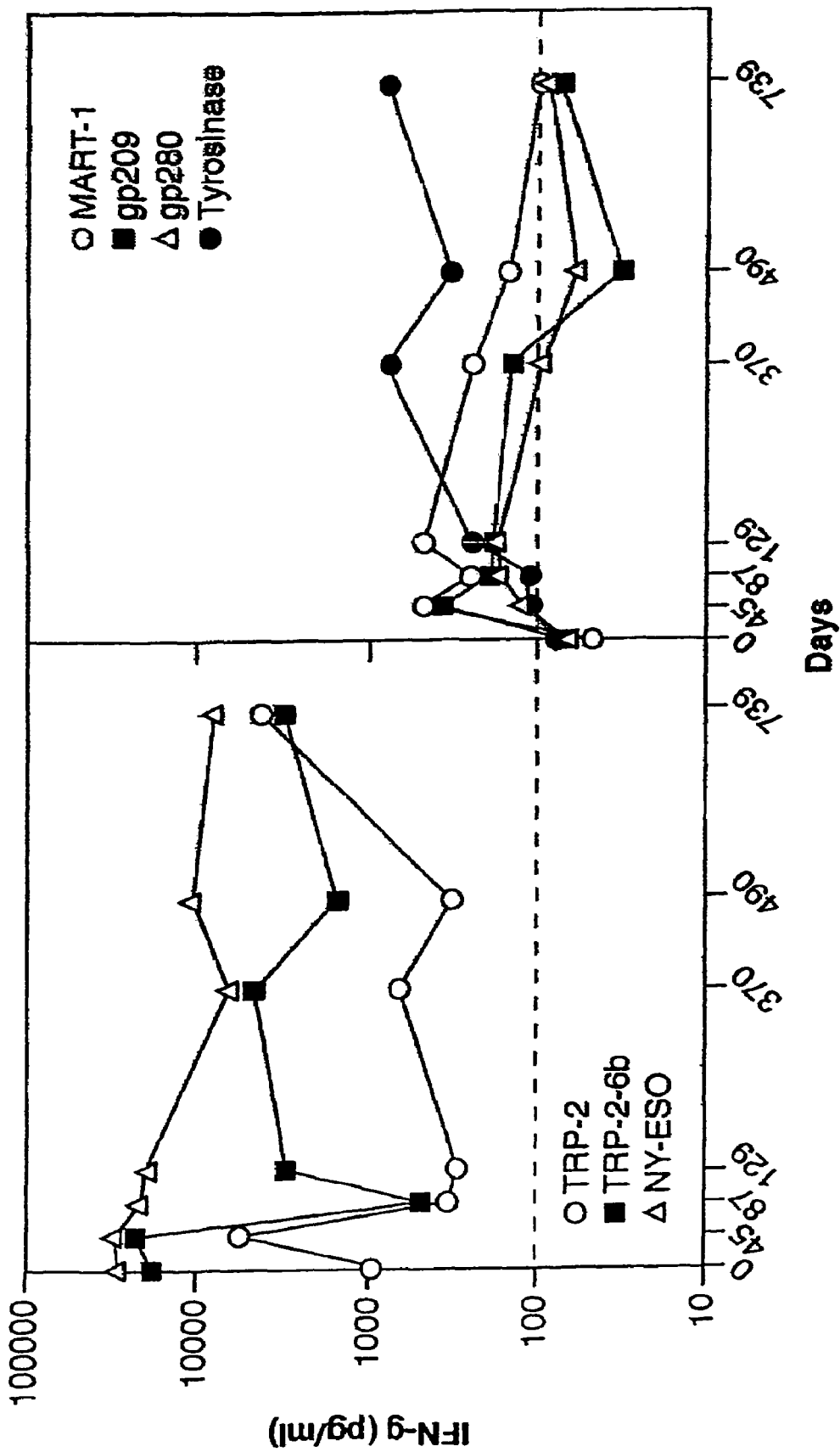
FIG. 4 shows immunologic reactivity to TRP2, TRP2-6b, NY-ESO, MART-1, gp209, gp280, and tyrosinase detected in the PBMC of patient MM prior to and during treatment as measured by a 12 day in vitro sensitization assay. On day 0, PBMC were obtained a few hours prior to her first vaccination with a 4-peptide mixture comprising: gp100:209-217 (210M); gp100:280-288 (288V); MART-1:27-35; and tyrosinase:368-376. On day 45, PBMC were obtained after 2 cycles of vaccination and immediately prior to the third treatment, which corresponded to tumor regression.

Immunologic Reactivity Against NY-ESO, TRP2, TRP2-6b, and Four Peptides Used for Vaccinating Patient MM Peripheral blood mononuclear cells from patient MM were collected prior to and during the course of treatment. They were further tested for reactivity against NY-ESO, TRP2, TRP2-6b, and the four peptides that she was initially immunized with, by stimulating the PBMC in vitro for 12 days with the epitopes from these antigens. The pre-treated PBMC (day 0) exhibited strong reactivity against NY-ESO and the two TRP2 isoforms, none of which she was vaccinated against. Surprisingly, the peak reactivity against NY-ESO and both TRP2 antigens observed in the PBMC samples occurred after 2 cycles of treatment (day 45), which corresponded to a dramatic regression in most of the patient tumors. However, the immune responses directed against MART-1, gp209, gp280, and tyrosinase, the peptides that the patient was originally vaccinated with, were not present in the pre-vaccination PBMC (FIG. 4). Accordingly, reactivity to gp100, MART-1, and tyrosinase developed after immunization with peptides from antigens.

Example 8

TRP2-6b Vaccines as Treatment for Melanoma in Mammals

TRP2-6b vaccines may be useful in treating mammals, preferably humans, afflicted with melanoma by administering said vaccine to individuals in need. TRP2-6b proteins, peptides, or derivatives thereof, can be used to immunize mammals as described herein comprising ranges of about 1 mg to about 100 mg. In another instance, mammals can be immunized with the TRP2 nucleic acid sequence inserted into a viral vector such as vaccinia virus, adenovirus, or fowlpox virus. About $10^6$ to about $10^{11}$ viral particles per mammal, preferably human, containing the TRP2-6b nucleic acid sequences corresponding to immunogenic TRP2-6b peptides or derivatives thereof can be administered. Further, mammals may be monitored for antibodies to the immunogen or an increase in CTLs recognizing the immunogens by either means well known in the art or alleviation of clinical signs and symptoms of the active disease. The production of immune cells recognizing the vaccine antigen or tumor regression are two parameters which are assessed. These vaccines may be used for prophylactic or therapeutic applications.

Example 9

Therapeutic Treatment of Mammals Afflicted with Melanoma Using Lymphocytes Reactive to Immunogenic Peptides The therapeutic treatment of mammals afflicted with melanoma may be effective using T lymphocytes presensitized to the melanoma antigen such as TRP2-6b. Isolated T lymphocytes are cultured in vitro (Kawakami, et al., J. Exp. Med. 168:2183-2191, 1988). Preferably the T lymphocytes are exposed to a TRP2-6b peptide, TRP2-6b:402-411 or TRP2-6b:403-411, for a sufficient period of time, such period ranging from 1 to 16 hours, at a concentration ranging from about 1 to about 10 mg/ml. Further, about $10^9$ to about $10^{12}$ melanoma antigen-reactive T lymphocytes can be administered to a mammal, preferably human. In another instance, the T lymphocytes may be exposed to the modified TRP2-6b peptides. Administration of such lymphocytes may be accomplished in a number of ways, but not limited to intravenously, intraperitoneally, or intralesionally. In addition, said T lymphocytes may be administered in conjunction with other therapeutic treatments, including cytokine, radiotherapy, chemotherapy, adoptive T lymphocyte therapy, and surgical excision of melanoma lesions.

The foregoing description of the specified embodiments will so fully reveal the general nature of the invention that others can, by applying knowledge within the skill of the art (including the contents of the references cited herein), readily modify, and/or adapt for various applications such specific embodiments, without undue experimentation, without departing form the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. An isolated protein comprising the 552 amino acids encoded by nucleotides 297-1951 of SEQ ID NO: 1.

2. An isolated polynucleotide comprising a nucleotide sequence encoding the protein of claim 1, optionally as part of an expression vector.

3. The isolated polynucleotide of claim 2, wherein the nucleotide sequence is SEQ ID NO: 1.

4. An isolated host cell comprising an expression vector comprising the polynucleotide of claim 2.

5. The isolated host cell of claim 4, wherein said cell is a T cell.

* * * * *

SEQUENCE LISTING

```
<160> NUMBER OF SEQ ID NOS: 4

<210> SEQ ID NO 1
<211> LENGTH: 2278
<212> TYPE: DNA
<213> ORGANISM: Homo sapiens
<220> FEATURE:
<221> NAME/KEY: CDS
<222> LOCATION: (1472)..(1570)

<400> SEQUENCE: 1
atggtgagaa gcgctaccct cattaaattt ggttgttaga ggcgcttcta aggaaattaa      60
gtctgttagt tgtttgaatc acataaaatt gtgtgtgcac gttcatgtac acatgtgcac     120
acatgtaacc tctgtgattc ttgtgggtat tttttttaaga agaaaggaat agaaagcaaa     180
gaaaaataaa aaatactgaa aagaaaagac tgaaagagta gaagataagg agaaaagtac     240
gacagagaca aggaaagtaa gagagagaga gagctctccc aattataaag ccatgagccc     300
cctttggtgg gggtttctgc tcagttgctt gggctgcaaa atcctgccag gagcccaggg     360
tcagttcccc cgagtctgca tgacggtgga cagcctagtg aacaaggagt gctgcccacg     420
cctgggtgca gagtcggcca atgtctgtgg ctctcagcaa ggccgggggc agtgcacaga     480
ggtgcgagcc gacacaaggc cctggagtgg tccctacatc ctacgaaacc aggatgaccg     540
```

-continued

```
tgagctgtgg ccaagaaaat tcttccaccg gacctgcaag tgcacaggaa actttgccgg    600
ctataattgt ggagactgca agtttggctg gaccggtccc aactgcgagc ggaagaaacc    660
accagtgatt cggcagaaca tccattcctt gagtcctcag gaaagagagc agttcttggg    720
cgccttagat ctcgcgaaga agagagtaca ccccgactac gtgatcacca cacaacactg    780
gctgggcctg cttgggccca atggaaccca gccgcagttt gccaactgca gtgtttatga    840
ttttttttgtg tggctccatt attattctgt tagagataca ttattaggac caggacgccc    900
ctacagggcc atagatttct cacatcaagg acctgcattt gttacctggc accggtacca    960
tttgttgtgt ctggaaagag atctccagcg actcattggc aatgagtctt ttgctttgcc   1020
ctactggaac tttgccactg ggaggaacga gtgtgatgtg tgtacagacc agctgtttgg   1080
ggcagcgaga ccagacgatc cgactctgat tagtcggaac tcaagattct ccagctggga   1140
aactgtctgt gatagcttgg atgactacaa ccacctggtc accttgtgca atggaaccta   1200
tgaaggtttg ctgagaagaa atcaaatggg aagaaacagc atgaaattgc caaccttaaa   1260
agacatacga gattgcctgt ctctccagaa gtttgacaat cctcccttct tccagaactc   1320
taccttcagt ttcaggaatg ctttggaagg gtttgataaa gcagatggga ctctggattc   1380
tcaagtgatg agccttcata atttggttca ttccttcctg aacgggacaa acgctttgcc   1440
acattcagcc gccaatgatc ccattttttgt g gtg att tct aat cgt ttg ctt       1492
                                    Val Ile Ser Asn Arg Leu Leu
                                     1               5
tac aat gct aca aca aac atc ctt gaa cat gta aga aaa gag aaa gcg     1540
Tyr Asn Ala Thr Thr Asn Ile Leu Glu His Val Arg Lys Glu Lys Ala
        10              15              20
acc aag gaa ctc cct tcc ctg cat gtg ctg gttcttcatt cctttactga       1590
Thr Lys Glu Leu Pro Ser Leu His Val Leu
        25              30
tgccatcttt gatgagtgga tgaaaagatt taatcctcct gcagatgcct ggcctcagga   1650
gctggcccct attggtcaca atcggatgta caacatggtt cctttcttcc ctccagtgac   1710
taatgaagaa ctctttttaa cctcagacca acttggctac agctatgcca tcgatctgcc   1770
agtttcagtt gaagaaactc caggttggcc cacaactctc ttagtagtca tgggaacact   1830
ggtggctttg gttggtcttt ttgtgctgtt ggcttttctt caatatagaa gacttcgaaa   1890
aggatataca cccctaatgg agacacattt aagcagcaag agatacacag aagaagccta   1950
gggtgctcat gccttaccta agagaagagg ctggccaagc acagttctg acgctgacaa    2010
taaaggaact aatcctcact gttccttctt gagttgaaga tctttgacat aggttcttct    2070
atagtgatga tgatctcatt cagaagatgc ttagctgtag tttccgcttt gcttgcttgt    2130
ttaacaaacc caactaaagt gcttgaggct acctctacct tcaaataaag atagacctga    2190
caatttgtga tatctaataa taaccccccc cccaatattg attaagcctc ctccttttct    2250
gaaagcattt aaaaaaaaca aaaaaaa                                       2278
```

<210> SEQ ID NO 2
<211> LENGTH: 33
<212> TYPE: PRT
<213> ORGANISM: Homo sapiens

<400> SEQUENCE: 2

Val Ile Ser Asn Arg Leu Leu Tyr Asn Ala Thr Thr Asn Ile Leu Glu
1               5                   10                  15

His Val Arg Lys Glu Lys Ala Thr Lys Glu Leu Pro Ser Leu His Val

```
                    20                  25                  30
Leu

<210> SEQ ID NO 3
<211> LENGTH: 10
<212> TYPE: PRT
<213> ORGANISM: Artificial
<220> FEATURE:
<223> OTHER INFORMATION: Synthetic

<400> SEQUENCE: 3

Asn Ala Thr Thr Asn Ile Leu Glu His Val
1               5                   10

<210> SEQ ID NO 4
<211> LENGTH: 9
<212> TYPE: PRT
<213> ORGANISM: Artificial
<220> FEATURE:
<223> OTHER INFORMATION: Synthetic

<400> SEQUENCE: 4

Ala Thr Thr Asn Ile Leu Glu His Val
1               5
```